United States Patent [19]

Johnson

[11] 4,196,978

[45] Apr. 8, 1980

[54] BIOFOCAL TYPE OPHTHALMIC LENS ALIGNMENT DETERMINING DEVICE

[76] Inventor: D. Olin Johnson, 2104 Shenandoah Rd., Raleigh, N.C. 27602

[21] Appl. No.: 843,445

[22] Filed: Oct. 19, 1977

[51] Int. Cl.² .............................................. A61B 3/10
[52] U.S. Cl. .......................................... 351/5; 33/200
[58] Field of Search ............... 356/127, 172, 391, 388, 356/399, 397, 154, 138, 171, 124, 164; 351/5; 33/200

[56] References Cited

U.S. PATENT DOCUMENTS 2,414,871  1/1947  Harper ................................. 356/164

3,737,238  6/1973  Reiner et al. ......................... 356/171

*Primary Examiner*—John K. Corbin
*Assistant Examiner*—Bruce Y. Arnold
*Attorney, Agent, or Firm*—Mills & Coats

[57] ABSTRACT

In abstract a preferred embodiment of this invention is a biofocal type ophthalmic lens alignment determining device wherein the alignment of the biofocal segment lines can be comparatively read. This invention incorporates alignment platform and a light source which projects a specially designed grid network onto a viewing screen to read and thus allow adjustment of the biofocal segment lines, the binocular pupillary distance, and the monocular pupillary distance.

9 Claims, 7 Drawing Figures

BIOFOCAL TYPE OPHTHALMIC LENS ALIGNMENT DETERMINING DEVICE

This invention relates to ophthalmological devices and more particularly biofocal type ophthalmic alignment determining means.

Many people may resemble each other but very rarely are two people found who so closely resemble each other to be considered "look alikes." The same is true with ophthalmic alignment of the eyes. In any given individual, the monocular pupillary distance from the bridge of the nose to each eye may vary as well as the height of the pupillary segments. In other words very rarely is a person found who has a symmetrical face and whose eyes from one side to the other will not vary as far as distance from the bridge of the nose goes and as to height. Even though these variations are not noticeable to the average person, almost everyone has at least a fraction of a millimeter variation in eye height and distance.

In the past the alignment of spectacle type ophthalmic lens has been accomplished by use of a small metric ruler held adjacent the frames supporting the lens. This is at best a somewhat haphazard method of aligning a lens, particularly the segment or upper border of biofocal type lens.

Some attempts have been made to more accurately and expediently determine the segment and pupillary alignments of biofocal type spectacles by developing, measuring and aligning test apparatus. None of these prior known alignment methods, however, have proved satisfactoy either from an accuracy standpoint or time involved in determining the same.

After much research and study into the above mentioned problems, the present invention has been developed to provide a ready means for determining parallel disposition of the segment lines of biofocal lens as well as the binocular and monocular pupillary distances therebetween. This improved alignment means takes the guess work out of opticianry and provides for the accurate alignment of biofocal segments relative to the measurement of the user of the spectacles.

In view of the above, it is an object of the present invention to provide a device for accurately determining both segment line alignment as well as binocular and monocular pupillary distances in biofocal type spectacles.

Another object of the present invention is to provide an alignment verifying means for biofocal type spectacles.

Another object of the present invention is to provide a means for accurately verifying proper alignment of biofocal segments in spectacle frames as to horizontal and vertical distances.

Another object of the present invention is to provide a device for quickly determining or verifying, in biofocal type spectacles, the segment height of each lens, the horizontal disposition of each segment line, and the monocular and binocular pupillary distances thereof.

An even further object of the present invention is to provide a device for verifying biofocal segments as to horizontal alignment, and monocular and binocular pupillary distances with a relative simple and inexpensive device which is extremely accurate and yet uncomplicated to use.

Other objects and advantages of the present invention will become apparent and obvious from a study of the following description and the accompanying drawings which are merely illustrative of such invention.

Figure 1:
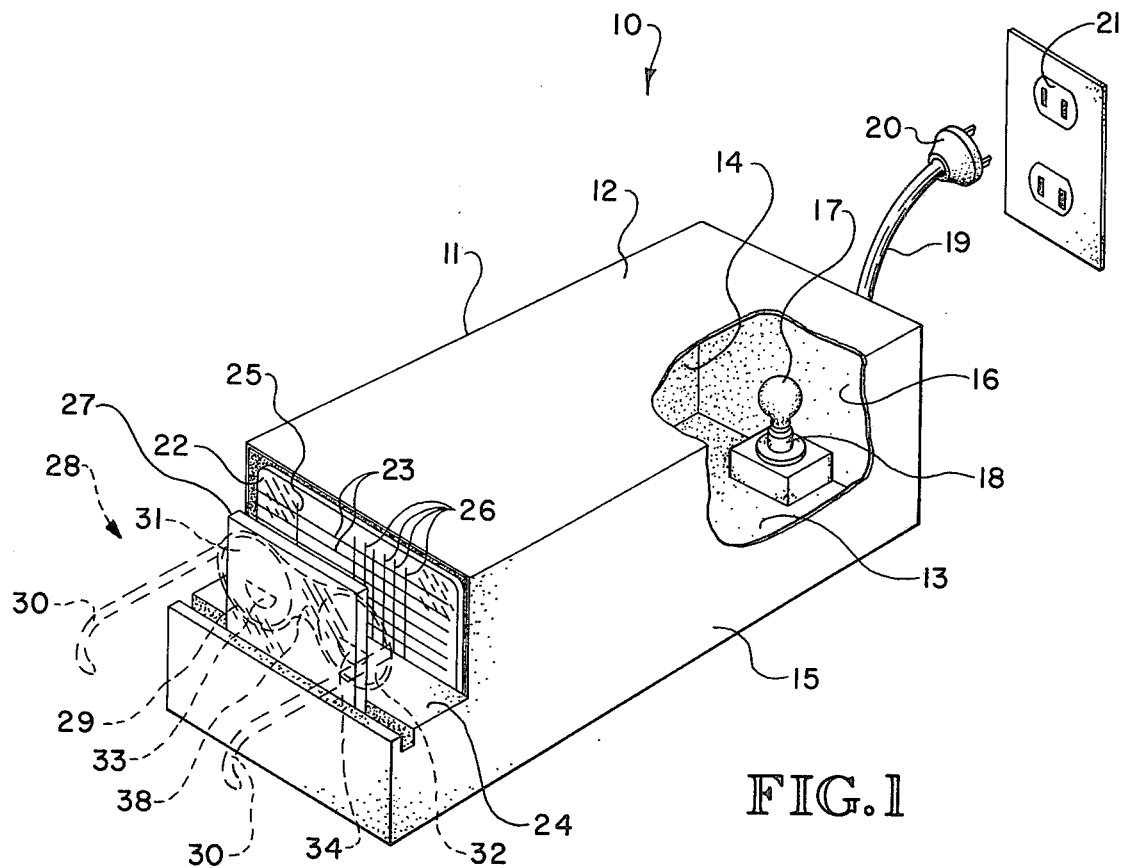
FIG. 1 is a perspective view of the biofocal type ophthalmic lens alignment determining device of the present invention.

With further reference to the drawings, the lens location determining device of the present invention indicated generally at 10 includes an elongated, preferably light impervious housing 11. This housing is composed of a top 12, bottom 13, sides 14 and 15, and a rear wall 16.

A light source 17 is provided adjacent rear wall 16 in housing 11 and can be in the form of an electric light bulb. If the light source is electrical, a bulb socket 18 is provided that is operatively connected to line cord 19 which terminates in plug 20. This plug is adapted to insertingly fit into electrical outlet 21 which is operatively connected to a power source (not shown).

Although not specifically shown, an electrical switch can be provided in line 19 is so desired.

The front of the elongated box-like housing 11 has a transparent face 22 with horizontal and vertical lines either etched or otherwise disposed thereon.

The horizontal lines are parallel to platform 24 and are preferably spaced in millimeters or increments thereof.

Transparent face 22 also includes a lens segment guide line 25 and a plurality of gross or binocular pupillary distance scales or lines 26. Again these lines or scales are preferably blocked off in millimeters or increments thereof.

Uprightly disposed in a plane generally parallel to transparent face 22 is a translucent projection screen 27.

Spectacles of the biofocal type are indicated generally at 28 and include a frame 29, temples 30, lens 31 and 32, and biofocal segments 33 and 34. Each of these last mentioned segments includes an upper portion which is generally linear and is referred to as segment lines 35 and 36.

To check the lens disposition or alignment within frame 29 of spectacle 28, such spectacles are rested on platform 24. Since the readings of the present device can be rapidly accomplished, no means is provided for holding the frame on the platform since the user of the device can readily either hold said frame or one of the temples 30. The view shown in FIG. 2 is what is seen by the operator (not shown) of the device of the present invention.

Figure 2:
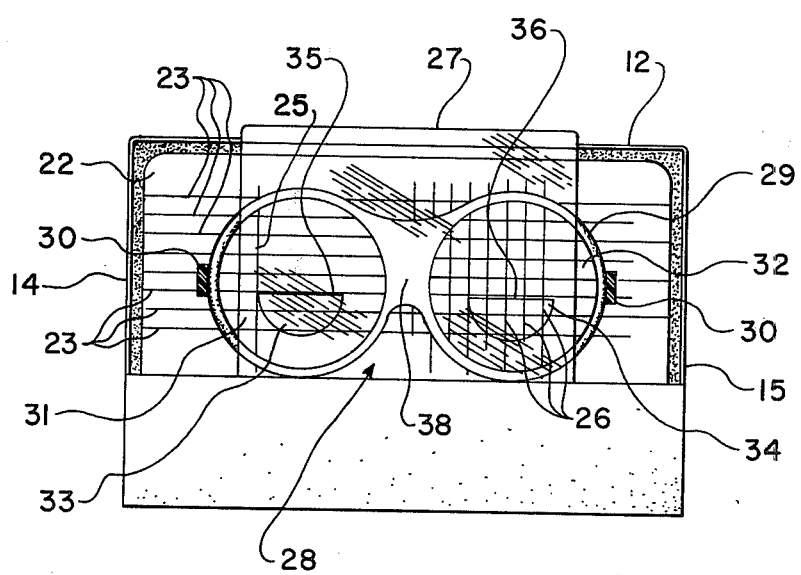
FIG. 2 is an end elevational view thereof showing spectacles in alignment determining position, the temples of such spectacles being shown in section for clarity.
Figure 3:
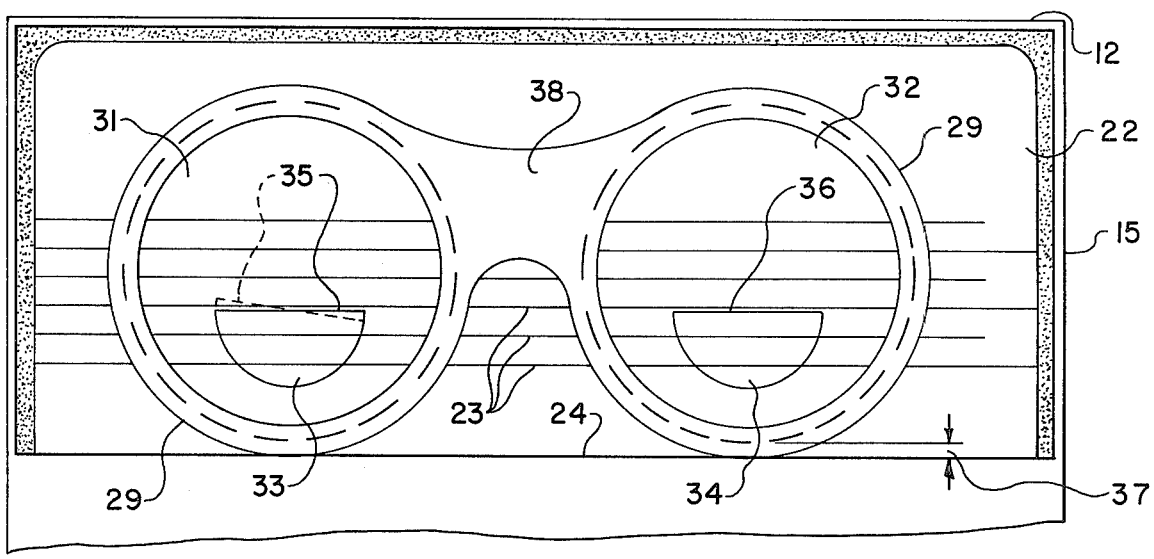
FIG. 3 is a front elevational view showing the method of horizontal alignment of the lens segments.
Figure 4:
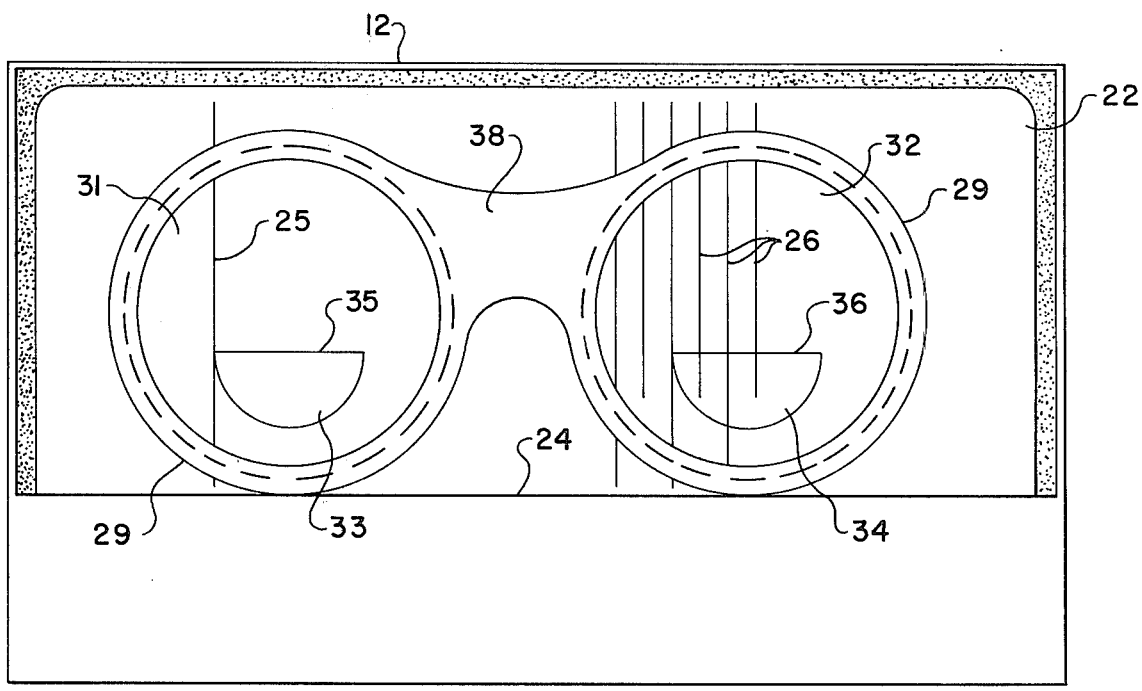
FIG. 4 is a front elevational view of the device showing the method of determining the segment binocular pupillary distance.
Figure 5:
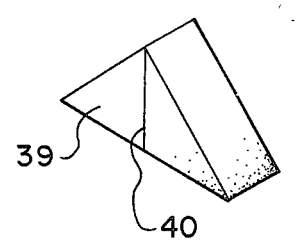
FIG. 5 is a perspective view of the centering prism.
Figure 6:
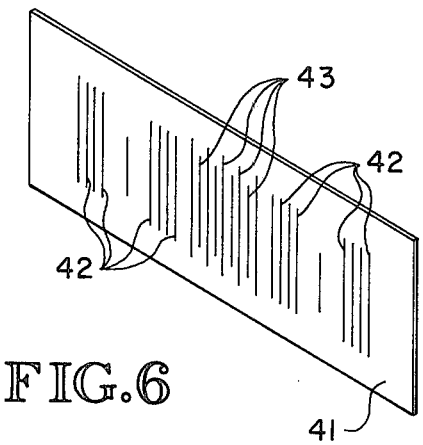
FIG. 6 is a perspective view of the binocular pupillary distance grid card.

For clarity of explanation, FIGS. 3 and 4 are illustrated separately but it is understood that the vertical and horizontal lines shown therein are seen together by the operator of the device as exemplified in FIG. 2.

To use the biofocal type ophthalmic lens disposition determining device of the present invention, light source 17 is illustrated in the conventional manner. The light passes through transparent face 22 causing shadows of the vertical and horizontal lines etched or otherwise disposed thereon to fall across and thus be projected onto translucent screen 27.

The spectacles 28 to be checked are then placed on platform 24 with the bottom of frame 29 resting thereon. The segment lines 35 and 36 of each of the biofocal segments 33 and 34 are compared to the projected horizontal lines 23 on screen 27. If the segment lines are not in horizontal parallel alignment, they will appear such as the left-hand segment 33 of FIG. 3. In such case the lens 31 would need to be rotated from the dotted position to the position shown in solid lines.

It should be noted at this point that the segment lines 35 and 36 should be in parallel horizontal alignment but not necessarily in actual alignment. The reason for this is that the eyes of many people are not in horizontal alignment. Thus the segment lines for any given person would have to be in parallel horizontal alignment but the actual alignment could be off.

Next, also using the horizontal lines 23, the net vertical height of each segment can be checked. This is accomplished by deducting the rim thickness indicated between the arrows at 37 from the height reading of the respective segment line in question.

To measure the pupillary distance, PD as it is referred to by those skilled in the art, one edge of biofocal segment 33 is aligned with segment guide line 25 as is seen clearly in FIGS. 2 and 4. Next the gross or binocular PD is read on scale lines 26, again as seen clearly in FIGS. 2 and 4. Some interpolation may, of course, be required but this is well within the capabilities of those skilled in the art. The reason, of course, the gross PD is checked is to make certain that the centers of the segments 33 and 34 are correctly spaced for the person for whom the spectacles are being prepared.

Also along this line, a monocular PD must be determined to make certain that the center of bridge 38 of frame 29 is at the proper location relative to the center of the segments. This is important for two reasons, first, if the eyes of the wearer (not shown) are equal distance from the bridge of the nose, the bridge of the frame must be equal distance between the center of the segments. If the wearer does not have a symmetrical face and one eye is further away from the bridge of the nose than the other, then that alignment must be taken into account in positioning the segments. Once the gross PD has been determined, then the monocular PD to either of the given segments is checked.

To check the monocular PD, the prism shaped frame support 39 with its etched center line 40 is placed on platform 24 adjacent screen 27. Transparent grid plate 41 is then placed between prism 39 and screen 27 with the bottom edge resting on platform 24.

Figure 7:
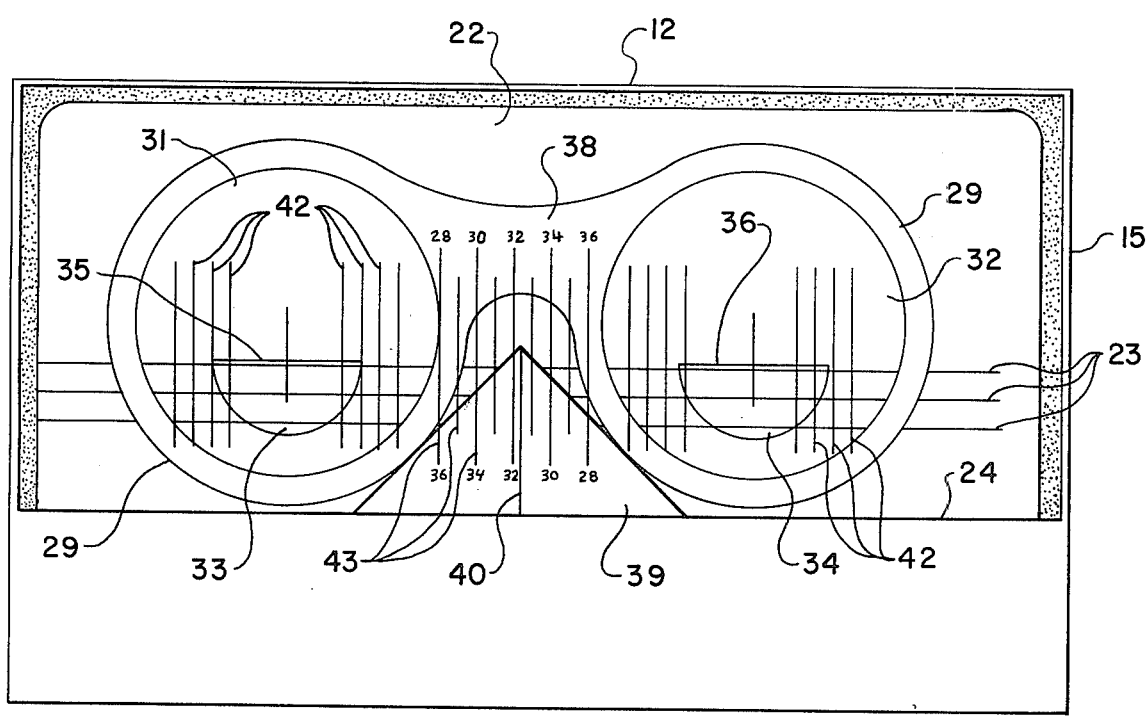
FIG. 7 is an elevational view showing the method of determining monocular pupillary distance.

As shown particularly clear in FIG. 7, segment 33 is centered by using the outer edges thereof in reference to centering lines 42 on plate 41. There are, of course, a plurality of these centering lines since the width of biofocal segments varies from one style spectacle to another.

Once segment 33 has been centered relative to lines 42, it is a simple matter to read the monocular PD on indicia lines 43 of plate 41 since center line 40 of frame support 39 will point to the center of bridge 38, the monocular PD being the distance from the center of such bridge to the center of any given biofocal segment.

If, of course, the binocular PD has been determined as hereinabove described, then once one of the monocular PDs has been determined, the other can be determined by subtracting the monocular PD from the gross or binocular PD. On the other hand, if it is desired to check the other monocular PD, grid plate 41 is reversed and the segment centering lines 42 placed adjacent segment 34. The PD can then be read as before using the prism center line 40 as a reference. This is the reason that the indicia lines 43 have metric distances marked out on both the top and bottom of lines 43.

Once the parallel alignment of the biofocal segments has been checked as well as the net vertical height of each segment and the gross and monocular PDs and these figures have been compared with the measurements taken from the person for whom the spectacles are being prepared, then the spectacles can be removed from the device and whatever adjustments, if any, made and then rechecked as required. Since there is no clamping or other holding means for the spectacles, the use of the device of the present invention can be accomplished very quickly and accurately without complicated manipulation.

From the above, it can be seen that the present invention has the advantage of providing a simple, relatively inexpensive and yet highly accurate means of checking the parallel alignment and net vertical height of biofocal segments as well as the gross and monocular PDs. This invention also has the advantage of being small enough to be placed in any convenient location in an optical laboratory and can be readily stored when not in use.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. An ophthalmic lens bifocal segment dispostion verification device comprising: a light source; a translucent screen disposed in spaced relation to said light source; a generally transparent member disposed between said translucent screen and said light source, said member having a plurality of horizontal and vertical lines marked thereon; and a platform disposed between said transparent member and said screen whereby when a pair of spectacles are disposed adjacent said platform between said member and said screen, said lines will be projected by said light source onto said screen to allow the disposition of said segments to be comparatively checked.

2. The device of claim 1 wherein said light source is enclosed within a housing.

3. The device of claim 2 wherein said housing is open at one end with said transparent member being disposed adjacent said opening.

4. The device of claim 1 wherein a generally prism shaped spectacle bridge centering means is provided.

5. The device of claim 1 wherein said marks are so disposed as to allow for determination of parallel alignment of spectacle biofocal segment lines.

6. The device of claim 1 wherein said marks are so disposed as to allow for determination of spectacle biofocal segment net vertical height.

7. The device of claim 1 wherein said marks are so disposed as to allow for determination of gross segment pupillary distance.

8. The device of claim 1 wherein a second transparent member having lines marked thereon is provided whereby when said second member is disposed between said light source and said screen, additional lines will be projected thereon.

9. The device of claim 8 wherein said marks are so disposed as to allow for determination of segment monocular pupillary distance.

* * * * *